United States Patent [19]

Binder et al.

[11] Patent Number: 5,416,023
[45] Date of Patent: May 16, 1995

[54] SYSTEM FOR BENZODIAZEPINE DETECTION

[75] Inventors: Steven R. Binder, Berkeley; David L. King, Benicia, both of Calif.

[73] Assignee: Bio-Rad Laboratories, Inc., Hercules, Calif.

[21] Appl. No.: 271,390

[22] Filed: Jul. 6, 1994

Related U.S. Application Data

[62] Division of Ser. No. 84,845, Jun. 29, 1993, Pat. No. 5,352,585.

[51] Int. Cl.$^6$ .......................................... G01N 30/02
[52] U.S. Cl. ................................... 435/288; 422/68.1; 422/70; 435/289; 435/291; 436/161; 436/178; 436/901; 436/504; 210/198.2; 210/656
[58] Field of Search ............... 436/161, 178, 174, 175, 436/177, 815, 901, 91, 92, 96–98, 106; 210/198.2, 283, 290, 635, 659, 656, 657; 435/18, 288, 289, 291; 422/70, 68.1, 83, 89

[56] References Cited

U.S. PATENT DOCUMENTS

| | | | |
|---|---|---|---|
| 3,625,652 | 12/1971 | Fujimoto et al. | 23/253 R |
| 3,901,655 | 8/1975 | Shukla et al. | 23/230 B |
| 4,056,468 | 11/1977 | Breiter et al. | 210/31 R |
| 4,204,952 | 5/1980 | Snyder | 210/31 C |
| 4,239,744 | 12/1980 | Paul et al. | 424/1 |
| 4,280,993 | 7/1981 | Braestrup et al. | 424/1 |
| 4,680,120 | 7/1987 | Ramsden et al. | 210/635 |
| 4,740,306 | 4/1988 | Litwack et al. | 210/198.2 |
| 4,828,799 | 5/1989 | Love et al. | 422/70 |
| 4,837,168 | 6/1989 | de Jaeger et al. | 436/533 |
| 5,057,437 | 10/1991 | Binder | 436/161 |

OTHER PUBLICATIONS

Fenton et al, a comparison of enzyme immunoassay and gas chromatographyl mass spectrometry in forensic toxicology, 1980, J. Forensic Sci, 25 (2), 314–19.
Von Meyer et al, Comparison of benzodiazepine screening ... in the low conc. range, 1988, Beitr. Gerichtl. Med. 46, 143–7.
Beck et al, Immunological screening of benzodiazepines in urine ... intake 1990, Toxicol, Lett. 52(1), 7–14.
Boukhabza et al., simple and sensitive ... liquid chromatography, 1990, J. Chromatogr., 529(1), 210–16.
Boppana et al., Immobilized sulfatase ... drug conjugates, 1989, J. Pharm. Sci, 78(2), 127–31.
Boppana et al., Immobilized sulfatase: beta.—glucumidase enzymes for the qualative ... drug conjugates, 1989, J. pharm Sci, 78(2), 127–31.
Mascher, separation, isolation and identification of optical isomers of ... reversed—phase HPLC, 1984, J. chromatogr. 306, 231–9.
Koike et al, Identification of Novel N-glucuronides in rat ... benzophenone derivative, 1986, J. Pharmacotolo—Dry 9(7), 578–84.

*Primary Examiner*—Jeffrey R. Snay
*Assistant Examiner*—Harold Y. Pyon
*Attorney, Agent, or Firm*—Townsend and Townsend Khourie and Crew

[57] ABSTRACT

Biological samples are analyzed for benzodiazepines in a single isocratic analysis using a chromatographic column system containing an immobilized enzyme reactor which cleaves glucuronic acid-conjugated benzodiazepines, an anion exchange column, a hydrophobic cation exchange column and a reverse-phase analytical column. Preferred methods of performing the analysis further involve the use of a hydrophobic cation exchange precolumn prior to the anion exchange column. The system readily lends itself to automation, automatic periodic sampling and benzodiazepine identification and quantification. The system is particularly well adapted to the determination and identification of benzodiazepines in urine samples.

19 Claims, 1 Drawing Sheet

SYSTEM FOR BENZODIAZEPINE DETECTION

This is a Division of application Ser. No. 08/084,845, now U.S. Pat. No. 5,352,585, filed Jun. 29, 1993.

This invention lies in the field of analytical systems and methods for biological fluids such as serum and urine. In particular, the technology to which this invention relates is that of chromatographic systems for automated drug analyses in biological fluids.

BACKGROUND OF THE INVENTION

Benzodiazepines are normally prescribed for therapeutic use, as tranquilizers, muscle relaxants, hypnotics, sedatives, treatments for insomnia, anticonvulsants, and the like. The variety of these drugs and their level of consumption by the public is increasing at a fast rate. They frequently become drugs of abuse, however, and can easily reach toxic levels when administered for purposes other than therapeutic. For this reason, it is frequently necessary to determine the presence, type and amount of benzodiazepines in samples of urine and other biological fluids.

A common method of analysis for benzodiazepines and benzodiazepine metabolites is thin-layer chromatography of urine samples. Other methods include high-performance liquid chromatography and gas chromatography. These analytical methods are complicated however by a number of factors. One of these is the fact that the primary benzodiazepine metabolites (i.e., glucuronides) are extremely polar compounds and are not easily extracted from biological fluids. Extraction can be facilitated by first reacting the samples with $\beta$-glucuronidase, but this reagent is not recovered during the analysis, and the reaction typically requires from 4 to 16 hours to complete. Also, the concentrations of analytes in biological fluids after therapeutic doses can be very low, in some cases less than 10 ng/mL, and as a result, extremely sensitive detectors are necessary in order to reduce the possibility of false negative results. A further difficulty is that most benzodiazepines have very similar chemical structures, and are difficult to separate using standard chromatographic techniques. Still further, it is difficult to identify the compounds based solely on data such as UV spectra and gas chromatography-mass spectroscopy data which is generated by typical chromatograph detectors. To summarize the problems encountered in benzodiazepine detection and identification, these are:

(1) labor intensive sample preparation;
(2) difficulty in achieving adequate separation of all compounds in the class;
(3) difficulty in achieving adequate sensitivity and specificity;
(4) high-cost detection systems; and
(5) the requirement for high levels of technical expertise.

SUMMARY OF THE INVENTION

The present invention provides a chromatographic system and method which combine several unique features permitting an accurate identification and quantification of a wide range of benzodiazepines present in a biological sample in an unusually short period of time by isocratic separation.

Among the unique features of this invention are a distinct combination and arrangement of contact and separation media, notably, a contact medium serving as an immobilized enzyme reactor to cleave glucuronic acid conjugates of the benzodiazepines and thereby release unconjugated benzodiazepines for analysis, an anion exchange medium and a hydrophobic cation exchange medium for removal of interfering species from the test sample, and a reverse-phase medium for the analytical separation of the benzodiazepines. All such media are preferably in the form of stationary phases held in flow-through columns as packed beds. In preferred embodiments of the invention, the column combination also includes an additional hydrophobic cation exchange medium as a pre-column preceding the anion exchange medium, the other hydrophobic cation exchange medium and the reverse-phase medium in the order of sample contact. The hydrophobic cation exchange medium in the pre-column is of stronger hydrophobic character than the hydrophobic cation exchange medium through which the sample passes upon emerging from the anion exchange medium. The pre-column lessens the burden on the remaining separation media by eliminating from the sample many interfering species such as inorganic salts, proteins, peptides and hydrophilic compounds.

In further preferred embodiments, the invention includes an automated system which combines detection and scanning elements with a library of known spectra and retention times, to identify and quantify each benzodiazepine as it emerges individually from the column system. Still further embodiments also provide for the automatic injection of a multitude of test samples in sequence, with full system regeneration and conditioning in between each sample.

These and other unique features which are described below provide the invention with the capacity to analyze a biological sample for benzodiazepines to a high degree of accuracy and in an unusually short period of time. Implementation of the invention in the form of an automated system permits full analyses to be performed unattended in less than one hour. Other advantages will become apparent from the description which follows.

BRIEF DESCRIPTION OF THE DRAWING

The attached drawing is a block flow diagram of a benzodiazepine detection system in accordance with the invention.

DETAILED DESCRIPTION OF THE INVENTION AND PREFERRED EMBODIMENTS

Figure 1:
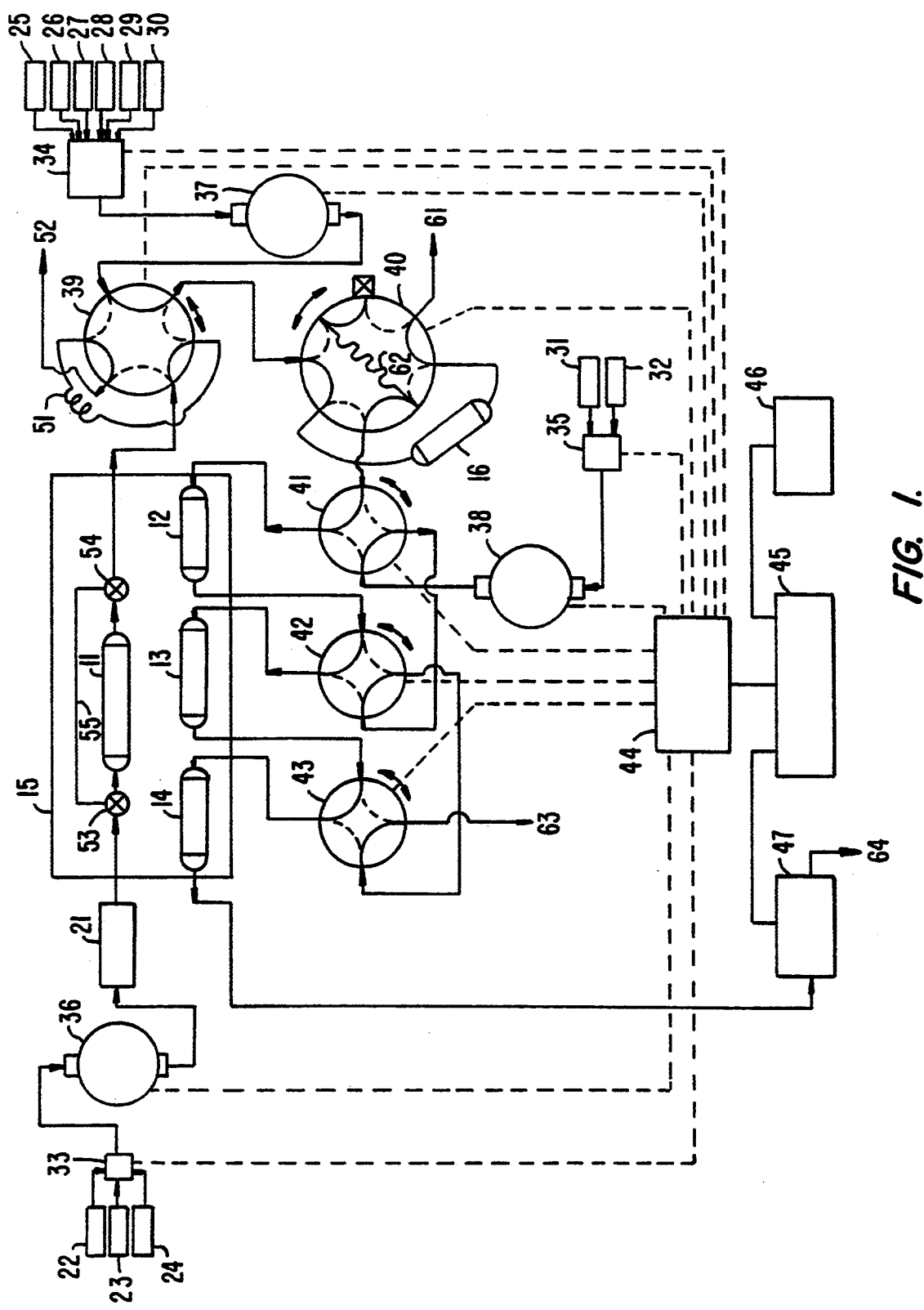

The term "benzodiazepines" is used in this specification and the appended claims to include both benzodiazepines and benzodiazepine metabolites. For those metabolites which are conjugates of a benzodiazepine with glucuronic acid, the term when applied to species downstream of the immobilized enzyme reactor refers to benzodiazepine metabolites from which any conjugated glucuronic acid has been removed.

The immobilized enzyme reactor is a reactor in which the test sample, conveyed by a carrier liquid, can be placed in contact with an immobilized glucuronosohydrolase. A preferred glucuronosohydrolase is $\beta$-D-glucuronide glucuronosohydrolase, also identified as $\beta$-glucuronidase EC 3.2.1.31. A preferred source of this enzyme is from the bacteria *Escherichia coli* (*E. coli*). One example of a preparation of this enzyme which can be readily obtained is Type IX-A, available from Sigma Chemical Company, St. Louis, Mo., U.S.A. (catalog no. G7396). Another example is Type X-A (Sigma catalog no. G7896), which is a more highly purified product.

Immobilization of the glucuronosohydrolase is achieved by chemically bonding the enzyme to a solid support through a linkage by conventional methods known to those familiar with methods of binding proteins to solid supports. The current level of skill in the art further permits one to readily select a binding method which will provide a stable linkage without causing denaturation of the enzyme. Further advantage in the context of this invention is gained by using a linkage which contains a cationic functional group. This increases the capacity of the support for the enzyme. Still further advantage is gained by selecting a hydrophilic linkage and a hydrophilic support. This will reduce the amount of non-specific binding of hydrophobic drug products to the support.

A preferred solid support for the purposes of the present invention is agarose. One example is an agarose gel bead such as Bio-Gel A-5M gel (Bio-Rad Laboratories, Inc., Hercules, Calif., U.S.A.). Attachment of the enzyme to this gel in a manner having the above characteristics is achieved by using an N-hydroxysuccinimide ester of the gel, available as AFFI-GEL-15 ® (Bio-Rad Laboratories, Inc., catalog no. 153-6052). The bead size of this gel is approximately 75–300 microns.

One example of an immobilization procedure is to mix an aqueous enzyme/salt solution with aqueous AFFI-GEL-15 at a low temperature for several hours, at a ratio within the range of 70 mg/mL to 80 mg/mL (weight of enzyme to volume of gel). The gel is then washed with any of various salt solutions to remove non-covalently bound enzyme. A blocking agent such as ethanolamine may also be employed. Enzyme immobilized in this manner will typically have an enzyme activity within the range of 70,000 to 100,000 modified Fishman units, as a measure of enzyme activity per mL of gel.

The immobilized enzyme reactor is preferably a flow-through column packed with the support-bound enzyme. The optimal reactor will be a cartridge designed to promote uniform contact of the mobile phase with the cartridge packing. One example of a cartridge of this type is that disclosed by Taylor, et al., in U.S. Pat. No. 4,871,463, issued Oct. 3, 1989, entitled "Vertical Reaction Vessel," incorporated herein by reference. For use in the present invention, a cartridge of this type may for example be packed with about one to five grams of the enzyme-bearing gel prepared in the manner described above.

The conditions under which enzymatic cleavage of the glucuronide conjugates will occur in this reactor will be readily apparent to those familiar with the enzyme. As one example, a biological sample such as urine is prepared by combining 1.0 mL of the sample with 0.5 mL of a buffer such as 0.1M sodium dihydrogen phosphate, thereby adjusting the pH of the sample to 6.9. For reasons related to the analysis to be performed downstream, at least one, and preferably two, internal standards will be included with the sample/buffer mixture. One of these standards can be a hydrophobic compound conjugated to glucuronic acid to confirm the effectiveness of the enzyme, and an example of the second standard is ethylnordiazepam, a synthetic compound not normally found in human biofluids.

The sample thus prepared is conveyed into the reactor by a further volume of the same pH 6.9 buffer at a flow rate of 0.1 to 1.0 mL/min. The sample travels with the buffer through the reactor, emerging from the reactor in hydrolyzed (unconjugated) form. To ensure the removal of all hydrolyzed product from the reactor, the reactor is then purged with an elution reagent containing 1–10% ethanol. Once this is done, the reactor may be reconditioned for another sample, by purging the reactor with the pH 6.9 buffer supplemented with 0.1 to 1.0M sodium chloride.

As indicated above, preferred embodiments of the invention include a hydrophobic cation exchange pre-column arranged for the sample to pass through prior to the entry of sample into the anion exchange medium. The pre-column is preferably positioned between the immobilized enzyme reactor and the anion exchange medium.

The pre-column contains a hydrophobic cation exchange medium selected to retain all species except inorganic salts, proteins, peptides and hydrophilic compounds. Once the salts, proteins, peptides and hydrophilic compounds are washed out of the column, the retained species, which consist of acids, bases and neutrals, including the benzodiazepines as well as other drugs and compounds, are eluted from the column. Of these eluted species, a neutral-to-weak-base fraction, including most benzodiazepines, is passed to the anion exchange medium, and an acid fraction is washed forward to waste and most bases are retained on the pre-column.

A suitable hydrophobic cation exchange medium for use for this purpose in the pre-column is a polymeric resin that has been modified to contain sulfonic acid functional sites. One example of a commercial product which can serve effectively as this medium is SHO-DEX ® DC-613, a sulfonated polystyrene gel having a particle size of approximately 6 microns. This product can be obtained from Showa Denko K. K., Tokyo, Japan. The column in which the medium is retained may vary widely in size and configuration. For a sample of the size indicated above, an appropriate column would be one measuring 10 mm (length)×4.0 mm (diameter).

Any of a wide variety of mobile liquid phases may be used to achieve the separation described above in the pre-column. The column is particularly effective, however, when a succession of mobile liquid phases of differing character are used. For example, the test sample emerging from the immobilized enzyme reactor may be first applied to the column with a low ionic strength aqueous buffer at a pH of 5–7, such as 5–100 mM sodium dihydrogen phosphate. Purging the column with an excess of this buffer will result in the removal of inorganic salts, proteins, peptides and hydrophilic compounds from the column, while the remainder, including the benzodiazepines, are retained. Acidic drugs such as barbiturates as well as other acidic compounds may then be removed by purging the column with an aqueous alkaline buffer. Preferred buffers of this type are those with a pH of about 10 to about 12, containing from about 1% to about 10% by weight of an alcohol such as methanol, ethanol or isopropanol. An example of such a buffer is a 50 mM disodium hydrogen phosphate/sodium hydroxide solution (pH 10.8) containing 5% ethanol (by weight).

Following the alkaline wash buffer, the next separation in the pre-column may be a separation on the basis of basicity to separate the benzodiazepines and other weakly basic compounds from the more basic compounds. To prepare the column for this separation, however, an aqueous acidic buffer may be passed through the column to enhance the cation exchange interaction of the basic drugs with the sulfonated resin. This will facilitate the subsequent basicity-based separation. Preferred such buffers are those with a pH of from about 4 to about 5.5. One example of an such a buffer is 50 mM sodium dihydrogen phosphate (pH 5). The selective elution of the less basic compounds (including the benzodiazepines) from the more basic is then achieved with a transfer buffer containing a high concentration of organic solvent. An example of such a buffer is 5 mM potassium dihydrogen phosphate (pH 7) containing 40% ethanol.

Reconditioning of the pre-column to remove the retained basic compounds is then achieved by purging with appropriate reagents, examples of which are 50 mM sodium hydroxide and methanol, ethanol or isopropanol, applied in succession, or a mixture of 75 parts methanol or ethanol with 25 parts 50 mM sodium hydroxide (20 mL).

The anion exchange medium retains hydrophobic anions, permitting other species which include the benzodiazepines to pass through. A preferred class of media for this purpose are polymeric resins containing quaternary ammonium functional sites. One example is styrene divinylbenzene derivatized to contain tetramethylammonium functional sites. One example of such a resin is AMINEX ® A-28 resin, available from Bio-Rad Laboratories, Inc. This resin has 8 % crosslinking and a particle size of about 11 microns.

The column in which the union exchange medium is retained may vary widely in size and configuration. For a biological sample of the size indicated above, an appropriate column would be one measuring 10 mm (length)×2.1 mm (diameter).

The hydrophobic cation exchange medium which succeeds the union exchange medium is a medium with a weakly hydrophobic character, and retains any basic compounds remaining in the sample which are of stronger basicity than benzodiazepines, with substantially no retention of the benzodiazepines. The benzodiazepines are thus freed of these interfering basic compounds, the benzodiazepines eluting from the column first and directed to the reverse phase column while later eluting basic compounds are directed to waste. A preferred class of media for this purpose are silicas bearing sulfonic acid functional sites. One example is silica with a particle size of approximately 5 microns, derivatized to contain propyl-sulfonic acid functional sites. An example of a derivatized silica of this type is Rainen C3-SCX, obtainable from Rainen Instrument Co., Woburn, Mass., U.S.A.

The column in which the weakly hydrophobic cation exchange medium is retained may vary widely in size and configuration. For a biological sample of the size indicated above, an appropriate column would be one measuring 30 mm (length)×3.2 mm (diameter).

As an alternative to using separate columns for the anion exchange medium and the weakly hydrophobic cation exchange medium, the two may be combined in a single column. This is achieved by mixing the two resins together in appropriate proportions and packing the mixture into a single column. To achieve results comparable to those of the examples given above, a suitable mixture would contain approximately 20% union exchanger and approximately 80% cation exchanger (by weight) in a total volume approximately equal to the total of those of the individual columns.

The benzodiazepines themselves are then chromatographically separated from each other for purposes of identification and quantification in a reverse-phase medium. Typical reverse-phase media may be used, with prominent examples being derivatized silicas, preferably those bearing alkyl functional sites. Alkyl groups of choice are those containing alkyl chains of 6 carbon atoms or more, preferably from about 6 to about 18 carbon atoms. In particularly preferred embodiments, the functional groups are attached by bonding the silica to a dimethylalkylsilane, in which the alkyl group is that referred to above. A variety of silicas of this description are commercially available. The carbon loading of the silica, i.e., the carbon atom content in weight percent, ranges from about 6% to about 12%, with about 8% to about 10% preferred. One example of a commercially available product effective for this purpose is ODS-HYPERSIL ®, a dimethyloctadecylsilane bonded to silica, a product of Shandon Scientific Ltd., distributed by Keystone Scientific, State College, Penn., U.S.A. This product has an average particle size of about 5 microns and an average pore size of about 120 Å.

As with all other media used in this invention, the reverse-phase medium will generally be retained in a packed column or cartridge which can vary widely in size and configuration. For a biological sample of the size referred to above, an example of a suitable column is one having a length of from about 100 mm to about 250 mm and a diameter of from about 4 mm to about 5 mm (for example, 4.6 mm).

Any of a wide variety of mobile phases may be used for eluting the benzodiazepines from the anion exchange column and hydrophobic cation exchange column (i.e., the weakly hydrophobic cation exchange column rather than the pre-column), and for the analytical separation in the reverse-phase column. To simplify the system, a common carrier liquid may be used for all three. For this purpose, a water-soluble organic solvent combined with an aqueous buffer at a pH of from about 6.0 to about 7.5 is preferred. Methanol, ethanol or isopropanol, at a concentration of from about 10% to about 50% by weight and an approximately neutral pH, are preferred. Methanol, ethanol or isopropanol at a concentration of from about 30% to about 50% by weight are particularly preferred. One example is a mixture of 40 parts by weight of ethanol with 60 parts by weight of an aqueous buffer containing 5 mM potassium dihydrogen phosphate, pH 7.0.

For the reverse-phase column, gradient elutions may also be used, and will in some cases provide a better separation. A typical gradient elution will involve a gradient in the alcohol concentration, rising from 20% to 70%, which is readily achieved by the use of two solutions supplied by separate reservoirs and combined with the use of a gradient mixing device of which various types are readily available from commercial sources.

The attached drawing is a block diagram illustrating an automated analytical system in accordance with the present invention, as an example embodying the principles described above.

Contained in a single housing within the system are the enzyme immobilization reactor 11, the anion exchange column 12, the weakly hydrophobic cation exchange column 13, and the reverse-phase column 14. The housing 15 is temperature-controlled at a constant temperature of about 32° C. The pre-column 16 is outside the housing and is operated at ambient temperature.

The column dimensions and packings for all columns in this example are the specific examples given above.

The system further contains an automated sampler 21 which draws precisely measured aliquots of each of a series of test samples in succession, and injects them into the flowing carrier liquid stream feeding the column system at preselected intervals. Conventional equipment designed for serial sample injection and which is suitable for use in this system is commercially available. In a typical automated sampler, the sample volume may vary from less than 100 μL to 5.0 mL. A preferred sample volume is 1.0 mL. Still further components of the system are a series of liquid reservoirs 22, 23, 24, 25, 26, 27, 28, 29, 30, 31, 32 which contain the various buffers, wash solutions and reconditioning agents used for achieving the separations and treating the column packings during the operation of the system, and three selector valves 33, 34, 35 which select among these liquids at various times throughout the protocol. Movement of the liquids through the columns is achieved by a series of pumps, including a peristaltic pump 36 upstream of the automated sampling device 21 and the immobilized enzyme reactor 11, and two high pressure pumps 37, 38, one 37 to drive liquids through the pre-column 16 and the other 38 to drive liquids through the remaining columns. A series of two-position switching valves 39, 40, 41, 42, 43 enable the system to direct the various liquids through the columns in the selected order and to separate the eluting fractions according to retention time so that undesired fractions can be directed to waste. The manipulations of the selector valves 33, 34, 35, the positions of the switching valves 39, 40, 41, 42, 43, and the activation and de, activation of the pumps 36, 37, 38 are all coordinated and controlled by a centralized system controller 44, which also controls a computer/monitor 45, printer 46 and detector 47. All of this equipment is commercially available and widely used in the industry for the same or similar functions.

A typical protocol for using this system in an automated sequence of steps is as follows.

The protocol begins with the first selector valve 33 in position to draw from the reservoir 22 which contains the pH 6.9 buffer (0.1M sodium dihydrogen phosphate). The peristaltic pump 36 draws the buffer and passes it through the automated sampling device 21 to flush a preset volume (such as 0.1 mL to 1.0 mL) of sample, which the buffer then carries through the immobilized enzyme reactor 11 at a rate of between 0.1 and 1.0 mL/min. As the hydrolyzed sample exits the immobilized enzyme reactor, it enters a retaining loop 51 through a six-port two-position switching valve 39 while the latter is in the position shown by the solid lines in the drawing. The retaining loop 51 has a capacity of from 2 mL to 7 mL, and loop overflow is directed to waste 52. The first selector valve 33 is then switched to draw from the second reservoir 23 which contains a stronger elution reagent such as 1-10% ethanol, which is then pumped through the immobilized enzyme reactor 11 to remove any remaining hydrolyzed drug product. The appropriate volume of the reagent pumped through the reactor will be from about 1.0 to about 6.0 mL. The entire hydrolyzed sample now resides in the retaining loop 51. At this point, the six-port two-position switching valve 39 is moved to the position indicated by the dashed lines. The first selector valve 33 is then switched to draw from the third reservoir 24 which contains a conditioning reagent to recondition the immobilized enzyme reactor 11 for the next sample.

Diverter valves 53, 54 are positioned on either side of the immobilized enzyme reactor 11, connected by a bypass line 55. By use of these valves and the bypass line, a test sample can bypass the immobilized enzyme reactor 11 and be loaded directly into the retaining loop 51. In an alternative design which is not shown in the Figure, a recycle line extending from the downstream diverter valve 54 back to a fourth position on the selector valve 33 may be used to recycle the test sample through the immobilized enzyme reactor 11, thereby increasing the contact time between the test sample and the enzyme.

With the hydrolyzed sample held in the retaining loop 51, the six-port two-position switching valve 39 in the position indicated by the dashed lines, and the second selector valve 34 in position to draw an application buffer 25, the first high pressure pump 37 is energized. The application buffer 25 is the low ionic strength aqueous buffer such as 5–100 mM sodium dihydrogen phosphate (pH 5–7). About 25 mL of this buffer is passed through the retaining loop 51, flushing the loop of the hydrolyzed sample. With the eight-port two-position switching valve 40 in the position indicated by the solid lines, the hydrolyzed sample passes directly into the pre-column 16, where the benzodiazepines together with various hydrophobic basic drugs, hydrophobic acidic drugs and hydrophobic neutral compounds are retained. The unretained components of the sample pass through to waste 61. Note that the transfer line 62 is not part of the switching valve 40 and does not rotate with the valve.

Once the full volume of application buffer has passed through the pre-column, the second selector valve 34 is switched to engage the liquid reservoir 26 containing the alkaline wash buffer. About 1 to 5 mL of the wash buffer is passed through the pre-column to eliminate or reduce the amounts of acidic drugs such as barbiturates which are endogenous to the sample. The second selector valve 34 is then switched again, to engage the liquid reservoir 27 containing the aqueous acidic exchange buffer. About 1.3 mL of this buffer is passed through the pre-column to enhance the interaction of the basic drugs with the sulfonated resin.

This is followed by a further switch of the second selector valve 34, this time to engage the liquid reservoir 28 containing the transfer buffer which will elute the benzodiazepines and other retained species from the pre-column and pass it through the anion exchange column 12. The preferred transfer buffer for this elution is an aqueous buffer containing 5 mM potassium dihydrogen phosphate, pH 7.0, plus 40% ethanol by weight. As the second selector valve 34 is switched, the eight-port two-position switching valve 40 is also switched to the position indicated by the dashed lines. With the first of the three four-port two-position switching valves 41 in the position indicated by the solid lines, the transfer buffer will thereupon draw the eluting species out of the pre-column and into the anion exchange column 12. A volume of 3 mL of the transfer buffer will suffice to achieve this transfer. Note that the direction of flow of the transfer buffer through the column is the reverse of that of the application buffer, alkaline wash buffer and acidic exchange buffer. The benzodiazepines and other retained species are thus back-flushed from the pre-column for a more efficient removal.

Once all of the retained species have passed from the pre-column 16 into the anion exchange column 12, the eight-port two-position switching valve 40 is switched back to the position indicated by the solid lines, and the second selector valve 34 is switched to engage the next two liquid reservoirs in succession, i.e., those containing the 50 mM sodium hydroxide 29 and the methanol 30, for reconditioning the pre-column. The passing of 3 mL each of these agents will provide proper reconditioning. With the switching valve 40 in this position, the reconditioning agents will pass through the column to waste 61. The second selector valve 34 is then switched back to the transfer buffer 28, and then to its initial position to provide the pre-column with a final flush with application buffer 25 to prepare it for the next sample.

With the remaining sample components now in the anion exchange column 12, the first four-port two-position switching valve 41 is switched to the position indicated by the dashed lines. With the third selector valve 35 in a position engaging the liquid reservoir containing further transfer buffer 31, the second high pressure pump 38 is activated, passing the transfer buffer 31 through the anion exchange column. This transfer buffer 31 may be the same as the first transfer buffer 28, but it is preferred to use one with a slightly higher buffer concentration, such as for example 40 pans by weight ethanol and 60 pans by weight 20 mM potassium dihydrogen phosphate, pH 7.0.

With the switching valve 41 and the selector valve 35 in these positions, sufficient transfer buffer, typically a volume of about 6 mL, is pumped through the column 12 to cause all of the sample components other than hydrophobic anions to pass through the column. While this is occurring, the second of the three four-port two-position switching valves 42 is in the position indicated by the solid lines, so that all species emerging from the anion exchange column 12 pass into the cation exchange column 13. The second switching valve 42 is then tuned to the position indicated by the dashed lines, the first switching valve 41 is returned to its solid-line position, and the eight-port two-position switching valve 40 is returned to its dashed-line position. The first transfer buffer 28 (typically about 6 mL) then passes through the anion exchange column 12, followed by the acid exchange buffer 27 (typically about 3 mL), then methanol 30 (typically about 3 mL) and then application buffer 25 (typically about 10 mL). During this sequence, the hydrophobic anions retained in the anion exchange column 12 elute from the column and pass through the last of the three four-port two-position switching valves 43, which is in the position indicated by the solid lines, to waste 63.

With the first switching valve 41 in the solid-line position, the second switching valve 42 in the dashed-line position, and the third switching valve 43 in the solid-line position, transfer buffer 31 is directed through the cation exchange column 13 into the reverse-phase column 14. The benzodiazepines, which act as neutral or extremely weak basic compounds in this system, exhibit only minimal retention in the cation exchange column 13, whereas the remaining compounds, which are weakly basic (but more so than the benzodiazepines), are retained. Once all of the benzodiazepines have passed through the cation exchange column 13 (approximately 3 mL), the eight-port valve 40 is returned to its solid-line position and the third switching valve 43 is switched to the dashed-line position, the retained basic compounds are eluted from the column. This is achieved by passing an additional 10 to 20 mL of transfer buffer 31 through the column. Alternately, about 3 mL of a stronger solvent 32 such as 50 mM sodium dihydrogen phosphate (pH 7) containing about 70% ethanol by volume can be used by proper selection of the solvent selector valve 35, followed by reequilibration with the transfer buffer 31.

During time periods when these columns are not in use, they can be individually reconditioned by directing the reconditioning agents 29, 30 through the columns to waste 63 in the same manner as these agents are used to recondition the pre-column 16. With the various switching valves 39, 40, 41, 42, 43 in appropriately selected positions and both high pressure pumps 37, 38 operating simultaneously, reconditioning of columns not in use can be performed at the same time that chromatographic separations are occurring in the others.

Once all benzodiazepines have been transferred to the reverse-phase column 14, the switching valves are arranged such that the first and second of the four-port valves 41, 42 are in their solid-line positions and the third is in its dashed-line position. Chromatographic separation of the benzodiazepines then occurs in the reverse-phase column, with the transfer buffer 31 as the mobile phase. The benzodiazepines emerge from the column fully separated and ready for detection. The emerging stream passes through a scanning ultraviolet spectrophotometric detector 47. This unit consists of conventional instrumentation which detects the peaks as they emerge using standard chromatographic detection methods. The unit also performs a UV absorptivity scan of each peak, preferably at multiple points on the peak, such as at the midpoints of the leading and trailing sides as well as the apex of the peak itself. Fluids which have passed through the detector are then passed to waste 64.

It will be apparent from the above description that the system shown in the Figure is designed for simultaneous chromatography and column washing. Alternately, each of the columns 12, 13, and 14 can be rinsed and reequilibrated independently by the pump 38 at the end of each run.

The information obtained in the detector 47 is monitored and processed by the computer/monitor unit 45. This unit contains a memory library of retention times and UV absorptivity scans for benzodiazepines, and compares the data received from the detector with the library information as a means of establishing the identity of each benzodiazepine passing through the detector 47. The computer/monitor 45 further integrates the peaks to provide information regarding the relative amounts of the benzodiazepines present in the sample. Thus, for each benzodiazepine in the sample, the system determines its identity (by UV scan and retention time) and its quantity (by peak integration and comparison with the internal standards). This information is then transmitted to the printer 46, which provides a full printed analysis of the benzodiazepines in the sample.

The following is a list of benzodiazepines and metabolites for which a sample of serum or urine may be analyzed by use of the system described above. This list is merely illustrative and is not intended to be comprehensive.

alprazolam
7-aminoclonazepam
7-aminoflunitrazepam
7-aminonitrazepam
bromazepam
chlordiazepoxide
clonazepam demoxepam
desalkylflurazepam
desalkyl-3-hydroxy-flurazepam
desmethylchlordiazepoxide
diazepam
estazolam
fludiazepam
flunitrazepam
4-hydroxyalprazolam
α-hydroxyalprazolam
α-hydroxyalprazolam glucuronide
hydroxyethylflurazepam
3-hydroxyprazepam
4-hydroxytriazolam
α-hydroxytriazolam
lorazepam
lorazepam glucuronide
nitrazepam
norflunitrazepam
oxazepam
oxazepam glucuronide
prazepam
temazepam
temazepam glucuronide
triazolam It will be readily apparent to those skilled in the art that numerous variations, modifications and substitutions may be made among the various units, columns, transfer line and valve arrangements, procedures, materials and other components of the system and method described above without departing from the spirit and scope of the invention.

What is claimed is:

1. A system for analyzing a biological sample for the presence of benzodiazepines, said system comprising:
   a column combination comprising:
   (i) a contact medium comprised of an immobilized glucuronosohydrolase;
   (ii) an anion exchange medium;
   (iii) a hydrophobic cation exchange medium;
   (iv) a reverse-phase medium;
   means for passing said sample first through said contact medium, followed by said anion exchange, hydrophobic cation exchange and reverse-phase media in succession; and
   means for detecting said benzodiazepines individually upon their emergence from said reverse-phase medium;
   said means for passing said sample selected, and said column combination arranged, to promote the selective retention of hydrophobic anions, with substantially no retention of benzodiazepines, on said anion exchange medium, and the selective retention of basic compounds of stronger basicity than benzodiazepines, with substantially no retention of benzodiazepines, on said hydrophobic cation exchange medium.

2. A system in accordance with claim 1 in which said hydrophobic cation exchange medium is defined as a first hydrophobic cation exchange medium, said system further comprising a second hydrophobic cation exchange medium arranged to receive said sample prior to entry of said sample into said anion exchange medium, said second hydrophobic cation exchange medium of substantially stronger hydrophobicity than said first hydrophobic cation exchange medium, thereby promoting the separation of substantially all inorganic salts, proteins, peptides and hydrophilic compounds in said sample from the remainder of said sample.

3. A system in accordance with claim 2 in which said second hydrophobic cation exchange medium is a polymeric medium with sulfonic acid functional sites.

4. A system in accordance with claim 2 in which said second hydrophobic cation exchange medium is a sulfonated styrene gel.

5. A system in accordance with claim 1 in which said contact medium is β-D-glucuronide glucuronosohydrolase immobilized on an agarose gel.

6. A system in accordance with claim 1 in which said anion exchange medium is a polymeric medium with quaternary ammonium functional sites.

7. A system in accordance with claim 1 in which said anion exchange medium is a styrene-divinylbenzene resin with tetramethylammonium functional sites.

8. A system in accordance with claim 1 in which said hydrophobic cation exchange medium is a derivatized silica bearing sulfonic acid functional sites.

9. A system in accordance with claim 1 in which said hydrophobic cation exchange medium is a derivatized silica bearing propyl-sulfonic acid functional sites.

10. A system in accordance with claim 1 in which said reverse-phase medium is a derivatized silica bearing alkyl functional sites.

11. A system in accordance with claim 1 in which said reverse-phase medium is a dimethyl alkyl silane bonded to silica, in which said alkyl group contains at least 6 carbon atoms.

12. A system in accordance with claim 1 in which said reverse-phase medium is dimethyloctadecylsilane bonded to silica.

13. A system in accordance with claim 2 in which:
   said contact medium is β-D-glucuronide glucuronosohydrolase immobilized on an agarose gel;
   said second hydrophobic cation exchange medium is a polymeric medium with sulfonic acid functional sites;
   said anion exchange medium is a styrene-divinylbenzene resin with tetramethylammonium functional sites;
   said first hydrophobic cation exchange medium is a derivatized silica bearing propyl-sulfonic acid functional sites; and
   said reverse-phase medium is dimethyloctadecylsilane bonded to silica.

14. A system in accordance with claim 1 further comprising a carrier liquid for transfering components of said sample among said contact medium, said anion exchange medium, said hydrophobic cation exchange medium, and said reverse-phase medium.

15. A system in accordance with claim 14 in which said carrier liquid is an aqueous solution of a member selected from the group consisting of methanol, ethanol and isopropanol, at a concentration of from about 10% to about 50% by weight and containing a buffer to maintain the pH at approximately neutral.

16. A system in accordance with claim 14 in which said carrier liquid is an aqueous solution of a member selected from the group consisting of methanol, ethanol and isopropanol, at a concentration of from about 30% to about 50% by weight and containing a buffer to maintain the pH at approximately neutral.

17. A system in accordance with claim 1 in which said detecting means comprises:

means for automatically scanning each benzodiazepine emerging from said column combination to produce an absorption spectrum characteristic of each said benzodiazepine;

a library of presupplied spectra of known benzodiazepines; and means for automatically comparing spectra produced by said scanning means with said presupplied spectra to determine the identity of benzodiazepines emerging from said column combination.

18. A system in accordance with claim 1 in which said detecting means comprises:

means for automatically detecting retention times of said benzodiazepines as they emerge from said column combination;

a library of predetermined retention times for known benzodiazepines; and means for automatically comparing retention times so detected with said predetermined retention times to determine the identity of benzodiazepines emerging from said column combination.

19. A system in accordance with claim 1 in which said detecting means comprises:

means for automatically scanning each benzodiazepine emerging from said column combination to produce an absorption spectrum characteristic of each said benzodiazepine;

a library of presupplied spectra of known benzodiazepines and means for automatically comparing spectra produced by said scanning means with said presupplied spectra;

means for automatically detecting retention times of said drugs as they emerge from said column combination;

a library of predetermined retention times for known drugs and means for automatically comparing retention times so detected with said predetermined retention times; and peak integrating means for determining the relative amounts of said drugs in said sample as said drugs emerge from said column combination.

* * * * *